United States Patent
Gorelick

(10) Patent No.: US 9,685,251 B2
(45) Date of Patent: Jun. 20, 2017

(54) INTERFEROMETRIC DYNAMIC-GRATING IMAGING METHOD, DIFFRACTION GRATING AND IMAGING APPARATUS

(71) Applicant: Teknologian tutkimuskeskus VTT Oy, Espoo (FI)

(72) Inventor: Sergey Gorelick, Espoo (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 0 days.

(21) Appl. No.: 14/439,241

(22) PCT Filed: Oct. 28, 2013

(86) PCT No.: PCT/FI2013/051021
§ 371 (c)(1),
(2) Date: Apr. 29, 2015

(87) PCT Pub. No.: WO2014/068184
PCT Pub. Date: May 8, 2014

(65) Prior Publication Data
US 2015/0294749 A1    Oct. 15, 2015

(30) Foreign Application Priority Data

Oct. 29, 2012 (FI) .................................... 20126119

(51) Int. Cl.
*G03H 5/00*    (2006.01)
*G21K 1/06*    (2006.01)
(Continued)

(52) U.S. Cl.
CPC ............ *G21K 1/067* (2013.01); *A61B 6/4291* (2013.01); *A61B 6/484* (2013.01); *G01V 5/0016* (2013.01);
(Continued)

(58) Field of Classification Search
None
See application file for complete search history.

(56) References Cited

U.S. PATENT DOCUMENTS 5,999,319 A    12/1999 Castracane
6,643,065 B1 *    11/2003 Silberman ................. G01J 3/18
                                                                 359/230
(Continued)

FOREIGN PATENT DOCUMENTS

EP         2428830 A1    3/2012
JP      2005202013 A    7/2005
(Continued)

OTHER PUBLICATIONS

Pfeiffer, F et al: Phase retrieval and differential phase-contrast imaging wiht low-brilliance X-ray sources. Nature Physics, vol. 2, Aug. 2006.
(Continued)

*Primary Examiner* — Andrew Smyth
(74) *Attorney, Agent, or Firm* — Seppo Laine Oy

(57) ABSTRACT

The present invention relates to a method for producing an image of a target using radiation and a diffraction grating and apparatus for x-ray imaging. The method comprises directing a beam of radiation to the target to produce a modified beam through interaction with the target, directing the modified beam to an diffraction grating to produce an interference pattern, detecting the interference pattern using a detector, and forming an image of the target using the interference pattern measured. According to the invention, the diffraction grating is modified n the plane of the grating during the imaging so that at least two interference patterns are detected using the detector different configurations of the diffraction grating. Further, the image of the target using the at least two interference patterns measured. The invention (Continued)

provides a simple configuration, less radiation exposure and/or better image quality then conventional imaging methods.

15 Claims, 7 Drawing Sheets

(51) Int. Cl.
    *A61B 6/00*     (2006.01)
    *G21K 1/04*     (2006.01)
    *G01V 5/00*     (2006.01)
    *G02B 5/18*     (2006.01)

(52) U.S. Cl.
    CPC ............... *G21K 1/043* (2013.01); *G21K 1/06* (2013.01); *G02B 5/1838* (2013.01); *G21K 2201/067* (2013.01); *G21K 2207/005* (2013.01)

(56) References Cited

U.S. PATENT DOCUMENTS

| | | | |
|---|---|---|---|
| 6,985,294 B1 | 1/2006 | Rosenthal et al. | |
| 8,243,879 B2* | 8/2012 | Itoh | G21K 1/025 359/238 |
| 2007/0183563 A1 | 8/2007 | Baumann et al. | |
| 2010/0074395 A1* | 3/2010 | Popescu | A61B 6/06 378/16 |
| 2010/0246764 A1* | 9/2010 | Itoh | G21K 1/025 378/62 |
| 2011/0013743 A1* | 1/2011 | Nakamura | A61B 6/06 378/19 |
| 2011/0243305 A1* | 10/2011 | Tada | A61B 6/4291 378/87 |
| 2012/0057676 A1 | 3/2012 | Koehler et al. | |
| 2012/0099705 A1* | 4/2012 | Murakoshi | A61B 6/4291 378/85 |
| 2012/0106705 A1* | 5/2012 | Mikami | A61B 6/4233 378/70 |
| 2012/0114098 A1* | 5/2012 | Mikami | A61B 6/4233 378/62 |
| 2012/0183124 A1 | 7/2012 | Kaneko | |
| 2013/0208864 A1* | 8/2013 | Rossl | A61B 6/484 378/62 |

FOREIGN PATENT DOCUMENTS

| | | | | |
|---|---|---|---|---|
| WO | WO 2011096584 A1 * | 8/2011 | ........... | A61B 6/4233 |
| WO | WO2011096584 A1 | 8/2011 | | |
| WO | WO 2011157749 A1 | 12/2011 | | |
| WO | WO2012052881 A1 | 4/2012 | | |
| WO | WO2012081387 A1 | 6/2012 | | |

OTHER PUBLICATIONS

Rodriguez-Montero P et al: Adaptive photodetector for assisted Talbot effect. Applied Optics, Jul. 20, 2008.

Weitkamp, T et al: Xray phase imagin with a grating interferometer. Optics Express, vol. 12, No. 16, Aug. 8, 2005.

* cited by examiner

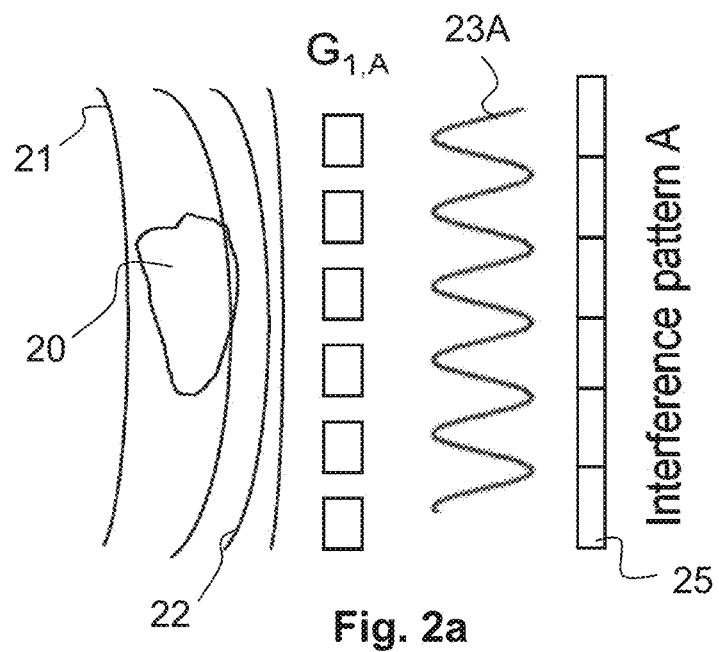
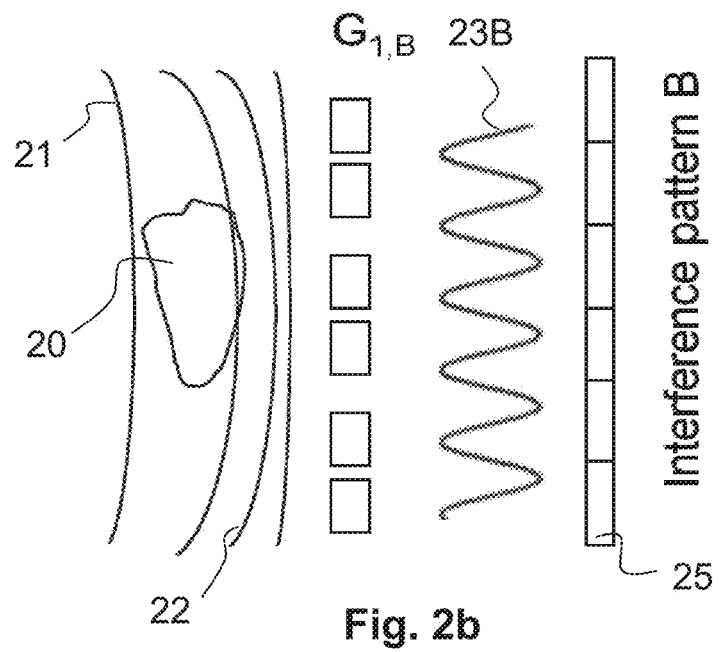

INTERFEROMETRIC DYNAMIC-GRATING IMAGING METHOD, DIFFRACTION GRATING AND IMAGING APPARATUS

FIELD OF THE INVENTION

The invention relates to radiation-based imaging, in particular to x-ray phase-contrast and dark-field interferometric imaging. The invention also relates to apparatuses suitable for carrying out the present method.

BACKGROUND OF THE INVENTION

X-ray imaging benefits from the ability of X-rays to penetrate through materials. Organic materials, such tumours, explosives or archeological artefacts, are largely transparent to high energy x-rays (wavelength >1 nm), and are therefore hard to image using traditional absorption contrast. Although high energy X-rays are weakly absorbed by materials, they are refracted, and this can be used to produce a phase-contrast image of objects. Phase-contrast image provides additional information on the internal structure of the object, and in case of organic materials this information can be more detailed than the absorption contrast. Additionally, interfaces and irregularities inside the imaged object scatter the x-rays, such that dark-field contrast carries even more information about the studied specimen. This additionally available phase- and dark-field contrast information can in some cases be much more detailed than in the case of the traditional absorption-contrast imaging, and can significantly improve diagnostics decision making, enhance failure analysis in material science, improve safety in airports by improved detection of forbidden organic substances (explosives, narcotics), benefit the geological studies (e.g., oil and diamond imaging), and wood/paper industry.

Grating-based interferometry is an established method for producing phase-contrast and dark-field contrast images. With reference to FIGS. 1a and 1b, in the method, a coherent beam 11 of light impinges on a diffraction grating $G_1$ and an intereference pattern 13A is formed behind the grating. At certain distances close to the grating, the intereference pattern resembles periodic structure of high and low intensities. If an organic object 10 (for instance tissue with a tumour) is positioned in the beam, the additional interaction of the beam 11 with the object 10 produces a modified beam 12, distorts the original periodic interference pattern 13A and produces a modified interference pattern 13B. A detector 15 can detect the distortions and the object's 10 image can be reconstructed. Usually the useful, object-related signals are weak and the image contrast is blurred by a large background. The useful signal is differentiated from the background by positioning an absorption grating $G_2$ in front of the detector 15. This grating $G_2$ completely absorbs the periodic intensities in the absence of the imaged object (see FIG. 1a). When the object is positioned in the beam 11, only the distortions due to the object are able to reach the detector 15 (see FIG. 1b).

Phase contrast microscopy allows imaging of transparent objects that are otherwise invisible in absorption contrast. Small phase variations are introduced into the propagating light, for example due to different refractive indices of neighbouring regions in the specimen, or due to their different densities. These small phase differences are translated into the variations of light intensity to visualize the transparent structures that would otherwise be invisible in absorption contrast. The access to the phase information can be obtained through a number of techniques. For the X-ray radiation, the most promising method is grating-based interferometry. In this method, a coherent X-ray beam impinges on a grating. The grating splits the beam into several components, that interefere with each other and produce periodic patterns in the near-field region. For a phase grating, i.e. (nearly) transparent grating that introduces a phase-shift into the incoming beam, with a phase-shift of π rad, the periodic patterns occur at certain distances $$d(N) = N \frac{1}{8} \frac{p^2}{\lambda}, N = 1, 3, 5 \ldots$$

For an absorption grating or a phase grating with a phase shift of π/2, the periodic patterns occur at distances $$d(N) = N \frac{1}{8} \frac{p^2}{\lambda}, N = 4, 8 \ldots$$

where p and λ are the periodicity of the grating and the wavelength, respectively. A phase object introduces additional variations into the primary beam such that the periodic near-field intereference pattern is distorted. An absorption grating is aligned in front of the detector, such that in the absence of an object, the grating absorbs the periodic pattern and no signal is detected. Due to the phase object, the interference fringes are shifted or distorted, such that some intensity is able to bypass the absorption grating and reach the detector.

To separate the object related phase shift information from other contributions, e.g. due to the imperfections of the illumination and the phase grating, the phase-stepping approach is used. One of the gratings, usually the absorption grating G2, is scanned over one period of the grating and for every point of the scan an image is taken. Usually, the similar procedure is repeated without the object to provide the background or reference signal to be subtracted from the images obtained with the object in the beam. For a sinusoidally varying signal on every pixel versus the grating shift, the minimum number of images that needs to be taken is three, or six images—if the reference images are taken too. However, to ensure a good quality of the image usually more images need to be taken.

Practically all currently available grating-based differential phase contrast methods rely on the use of absorption gratings to reduce the background and improve the image contrast. The grating is very expensive because it needs to be made of Au or other heavy material, needs to have a very fine pitch and be very tall. Further, the absorption grating limits the X-ray energy that can be used. Higher X-ray energies are beneficial for imaging of very thick specimens and help to reduce the radiation dose, e.g., in diagnostics imaging. Moreover, the signals are relatively low and the detector needs to integrate the intensities over long times. However, the image contrast of the resulting image is typically relatively low.

Grating-based differential phase-contrast imaging is discussed in more detail e.g. in Weitkamp et al, "X-ray phase imaging with a grating interferometer", Optics Express, Vol. 12, No. 16, 8 Aug. 2005 and Pfeiffer et al, "Phase retrieval and differential phase-contrast imaging with low-brilliance X-ray sources", nature physics, Vol. 2, April 2006.

There are also a plurality of variations of the basic method, including variations to the grating configurations.

Some of them are discussed in US 2011/0013743, US 2012/0057676 and US 2010/0246764. The last one of these describes a simplified fabrication method of an absorption source grating placed between the x-ray source and the object to be imaged, to improve the coherence of non-coherent X-ray sources. In addition, WO 2011/157749 discloses an inclining phase grating placed between the object and detector and having the advantage that it is suitable for different setups, energies, distances etc. without a need of making new gratings for every new setup. WO 2011/096584, on the other hand, discloses a "phase stepping" method where information about the shifts of interference fringes due to the refraction in the object is obtained by inclining or rotation of a grating in front of the detector.

The proposed variations still necessitate the use of a highly absorbing grating in front of the detector and therefore suffer from at least some of the same problems as the basic method. In addition, the contrast of the resulting images is not optimal, since the background image resulting from rays penetrating the absorption grating is still strong. Moreover, signal to noise ratios could be better. Also radiation doses are relatively high due to the low x-ray energies that need to be used.

In addition, the method does not provide a readily obtained phase contrast image. The object-phase-related image needs to be reconstructed (numerically) from a plurality of digital images.

Thus, there is a need for improved x-ray imaging methods and apparatuses.

SUMMARY OF THE INVENTION

It is an aim of the invention to provide a novel radiation, in particular x-ray radiation imaging method by which at least some of the problems indicated above can be avoided or diminished.

It is also an aim to provide a novel type of diffraction grating for x-ray phase-contrast and dark-field imaging and a novel x-ray imaging apparatus.

The aims of the invention are achieved by the invention as defined in the independent claims.

According to one aspect, the invention provides a method for producing an image of a target using x-rays, the method comprising directing a beam of x-rays to the target to produce a modified beam through interaction with the target, directing the modified beam to an diffraction grating to produce an interference pattern, detecting the interference pattern using a detector and computing an image of the target using the interference pattern measured. The diffraction grating is modified during imaging in the plane of the grating during the imaging so that at least two interference patterns are detected using the detector for different configurations of the diffraction grating. Finally, the computing step utilizes the at least two interference patterns measured for producing the image of the target. For the computing step there are also other options. For example, if a certain kind of detector is used, a ready image is formed on the detector without a need of computationally extracting it.

In other words, the diffraction grating is dynamic in order to produce dynamic interference, which is measured over time.

According to one embodiment, the dynamic modification comprises oscillation of the diffraction grating.

The modification of the diffraction grating may comprise one or both of the following actions done in the grating plane: modifying the period of the grating by moving at least some lines of the grating with respect to at least some other lines of the grating in the lateral plane of the grating, or translating the grating in the lateral plane of the grating. In the case of oscillating modification, these actions are done as a repeating sequence of movement or translation.

The grating is preferably kept in its original plane for the whole imaging period. In other words, the grating is not tilted.

According to one embodiment, the modifying comprises moving every second, every third or every fourth line of the grating with respect to intervening lines of the grating. As a result, the period configuration changes and a new interference pattern is formed.

The computing step preferably utilizes predefined information of the type of modification and geometrical details of the modification of the grating for producing the image of the target.

According to one embodiment, the method comprises reading the detector in synchronization with the modification of the diffraction grating in order to produce at least two different interference images corresponding to said at least two interference patterns, and computing the image of the target using said at least two interference images.

In an alternative embodiment, the method comprises integrating the at least two interference patterns on the detector over at least to produce an integrated interference image, and computing the image of the target using the integrated interference image.

The imaging sequence and image reconstruction may be carried in various ways and preferably information in the target is collected such that in computing stage there is sufficient information for reconstructing any of the following images: a phase-contrast image of the target, dark field-contrast image of the target, an absorption-contrast image of the target, one of both of the first two, however, being the ones which the present invention provides most improvement to.

In the most preferred form of the invention, the method comprises directing the interference pattern essentially directly from the diffraction grating to the detector, without intermediate gratings, and computing a phase-contrast image of the target. Thus, no absorption gratings are used. It should, however, be noted that considerable advantages are obtained even with the use of absorption grating.

In a preferred embodiment, the diffraction grating is made dynamic using MEMS technology, wherein the MEMS grating can be oscillated. The grating can be oscillated as a whole, or only every second finger, every third, every fourth, etc. fingers of the grating can be moved.

According to one embodiment, the diffraction grating comprises a microelectromechanically modifiable grating, preferably a silicon-based grating, which is adapted to diffract x-ray wavelengths. Such a grating is suitable for phase contrast or dark-field contrast x-ray imaging.

According to one aspect, the diffraction grating comprises a microelectromechanically modifiable device layer comprising a periodic pattern of grating lines, the period of the grating being adapted to diffract x-ray wavelengths, and means for changing the periodic configuration of the grating in response to electrical actuation.

According to one embodiment, the means for changing the periodic configuration comprise electrostatic or piezoelectric actuation means, which are as such known in the art. Detailed configurations will be described later.

According to one embodiment, a first portion of the grating lines is movable with respect to a second portion of grating lines in the plane of the grating for changing the periodic configuration. This can be implemented for example by arranging the grating lines in a comb configuration with two comb elements facing each other such that their grating lines (fingers) are interleaved with each other, and wherein at least one of said comb elements is movable in response to the actuation, the other one preferably being static.

In the abovementioned embodiment, the grating lines preferably maintain their original shape, i.e. being preferably straight, making the image reconstruction straightforward. An alternative implementation comprises grating lines which are bendable in response to said actuation. This also has an effect on the interference pattern and can be used to achieve the desired result although the computing may be more complex.

According to one aspect, there is provided an x-ray imaging apparatus capable of producing phase-contrast and/or dark-field contrast images, the apparatus comprising an x-ray source, an x-ray detector, a diffraction grating as described above arranged between the x-ray source and x-ray detector for producing an interference pattern on the x-ray detector, and means for computing an image of the target using the interference pattern measured.

Considerable advantages are achieved by means of the invention and its embodiments.

In contrast to static diffraction gratings according to the prior art, the present dynamic grating can be used to produce dynamic interference patterns. This at least the same information on the target than conventional static imaging techniques with a simple configuration, less radiation exposure or better image quality. By combing the dynamic gratings with interferometry techniques, the image parameters produced, such as intensity or position, become time-varying or, if the gratings oscillate, modulated. The low-noise and free from background image can be obtained by demodulating the signal. The oscillation can be, for example, sinusoidal.

Oscillation of the grating creates a time-varying interference pattern, and hence modulated signal on the detector pixels. If each pixel is able to lock-in on the modulated signal and demodulate the signal, the object-related signal and the static background can be differentiated thus improving the contrast, and furthermore, the noise levels can be significantly reduced.

To summarize, the main advantages of the invention and its embodiments comprise improved image contrast by filtering the static background and improved signal-to-noise ratio. Additionally, it can be used to simplify design of the interferometer (e.g. by leaving out the expensive absorption grating). In particular from living target's point of view, the possibility to reduce the radiation dose, e.g., in X-ray diagnostics and possibility to use higher X-ray energies, are remarkable benefits.

A further advantage of the invention is that it provides simpler extraction of absorption-, phase- and dark-field contrasts with the same setup, due to modulated diffraction grating. That is, the amount of information obtained by detecting the plurality of interference patterns is sufficient to be able to retrieve from the detected intensities differential phase contrast information, dark-field (scattered) signal and optionally also the absorption contrast, which all reflect different physical interactions of x-rays with the subject.

The invention can be used for simplified phase contrast imaging for example in x-ray diagnostics or materials science applications.

Embodiments of the invention are now described in more detail with reference to the attached drawings.

BRIEF DESCRIPTION OF THE DRAWINGS

FIGS. 2a and 2b illustrate dynamic grating-based interferometry according to one embodiment of the invention.

FIG. 5b is a zoom of the selected region from FIG. 5a.

DETAILED DESCRIPTION OF EMBODIMENTS

Practical implementations of the present novel approach based on dynamic diffraction gratings in particular for phase-contrast and dark-field imaging are introduced below. The disclosure is based on MEMS-technology gratings which can be actuated to change their periodicities.

FIGS. 2a and 2b illustrate the basic principle of the invention. In both figures, a wavefront 21 hits an object 20, producing a distorted wavefront 22. The distorted wavefront is directed to a grating $G_1$, which is shown in two different configurations $G_{1,A}$ and $G_{1,B}$, respectively, in the figures. In this example, every second grating line is moved. Consequently, different interference waves 23A and 23B, corresponding to the grating configurations $G_{1,A}$ and $G_{1,B}$, are produced and detected at the detector 25 as different interference patterns A and B, respectively. Similarly, every different grating configuration produces a different interference pattern, which may be detected.

Although shown in one dimension only, the measurement is typically made using a two-dimensional detector in order to be able to produce a two-dimensional image of the object.

It should be noted that in the embodiment shown, there is no absorption grating in front of the detector, but the interference pattern is detected directly.

Figure 1A:
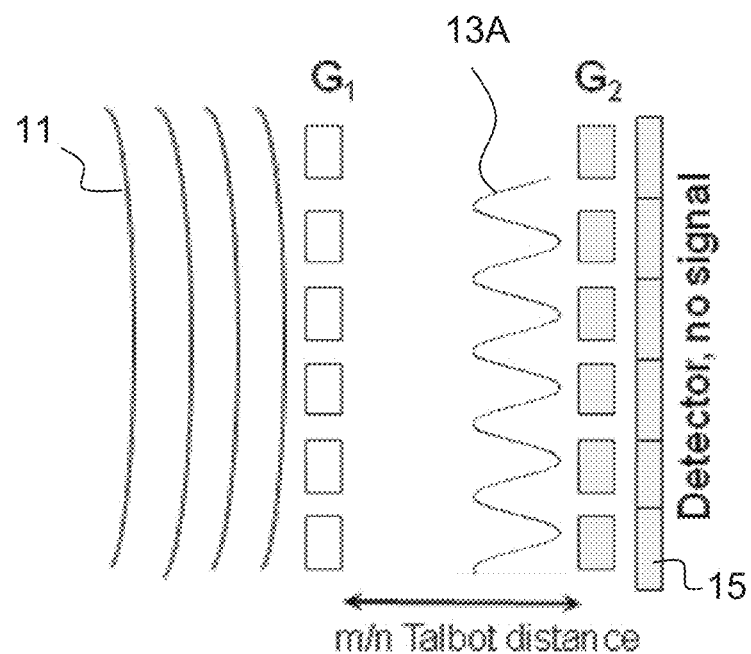
FIGS. 1a and 1b illustrate grating-based interferometry according to prior art.
Figure 1B:
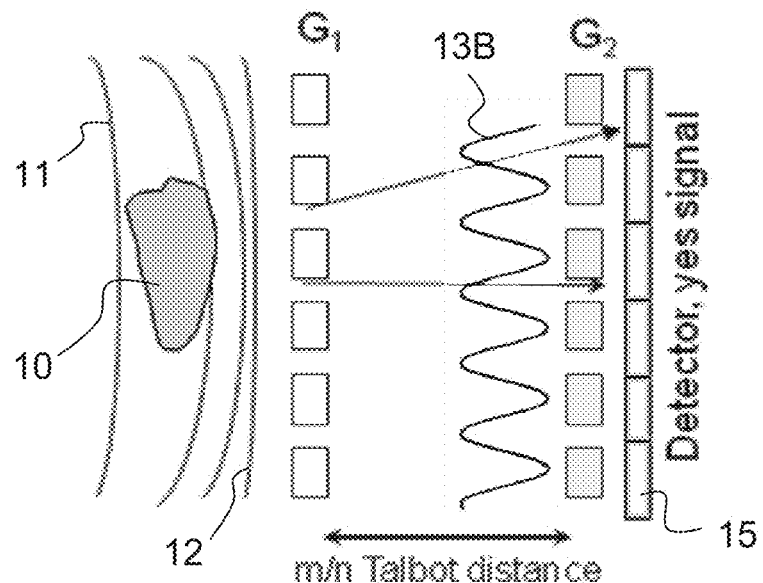
Figure 3A:
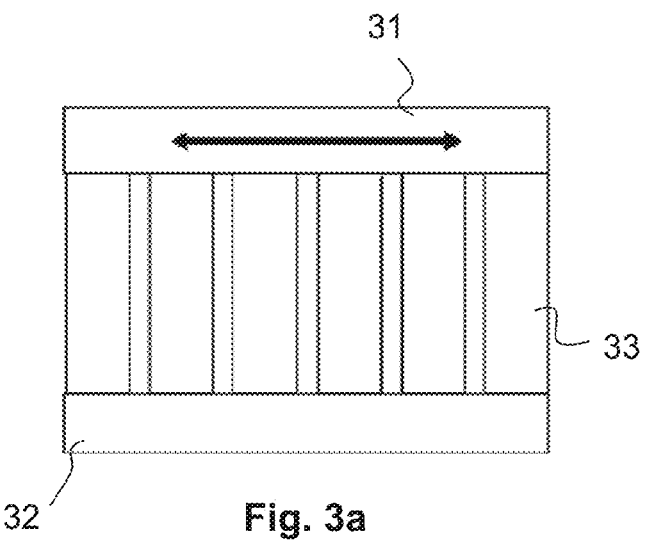
FIGS. 3a-3c show top views of dynamic gratings according to embodiments of the invention.

FIG. 3a illustrates a micromechanical grating structure. The structure comprises a first element, a second element 32 (optional) and a plurality of equally spaced fingers 33 (grating lines) attached to the first and second element and having a thickness (height), width and spacing sufficient to cause detectable interference of the x-ray beam used. The whole grating is arranged to move in a lateral direction perpendicular to the direction of the fingers 33 and perpendicular to the grating plane.

Figure 3B:
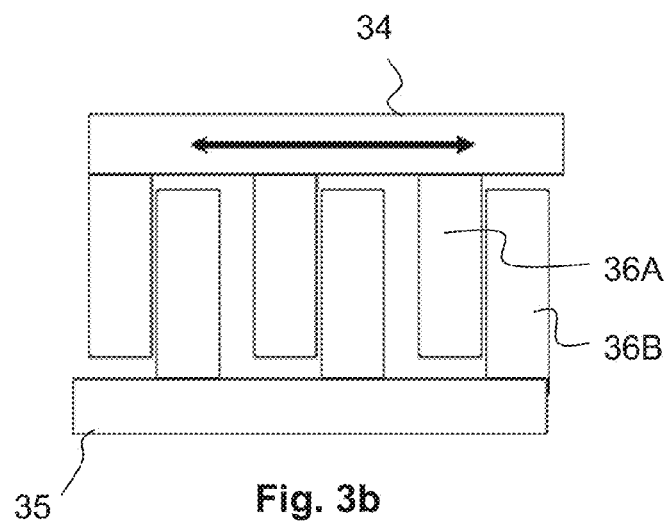

FIG. 3b shows another micromechanical grating structure as cross-sectional side view. The structure comprises a first element 34 having first fingers 36A attached thereto and a second element 35 having second fingers 36B attached thereto. The first and second fingers 36A, 36B are interleaved with each other so that when the first element 34 is moved, the grating configuration changes (every second finger gap is widened and every second narrowed). The fingers have a thickness (height), width and spacing sufficient to cause detectable interference of the x-ray beam used.

Figure 3C:
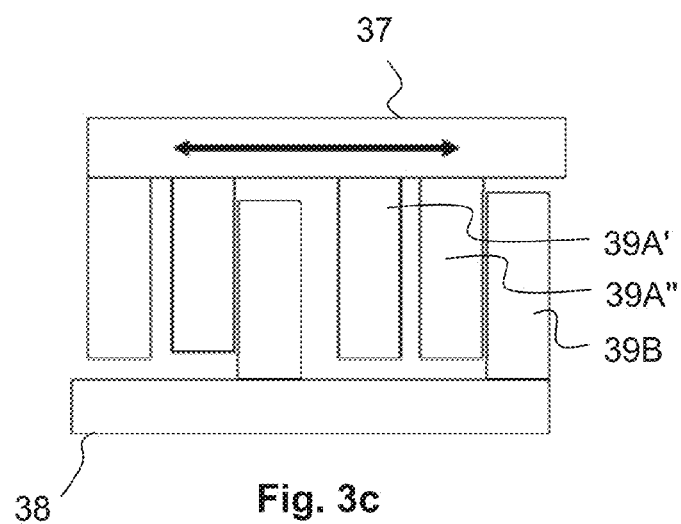

FIG. 3c shows a grating structure which is otherwise similar to that shown in FIG. 3b but herein there are two first fingers 39A', 39A" attached to the first element 37 for each second finger 39B attached to the second element 38. When the first element 37 and first fingers 39A', 39A" are moved, the gap configuration changes so that there are gaps of three different sizes, the one between the first fingers 39A', 39A" being static.

Figure 4A:
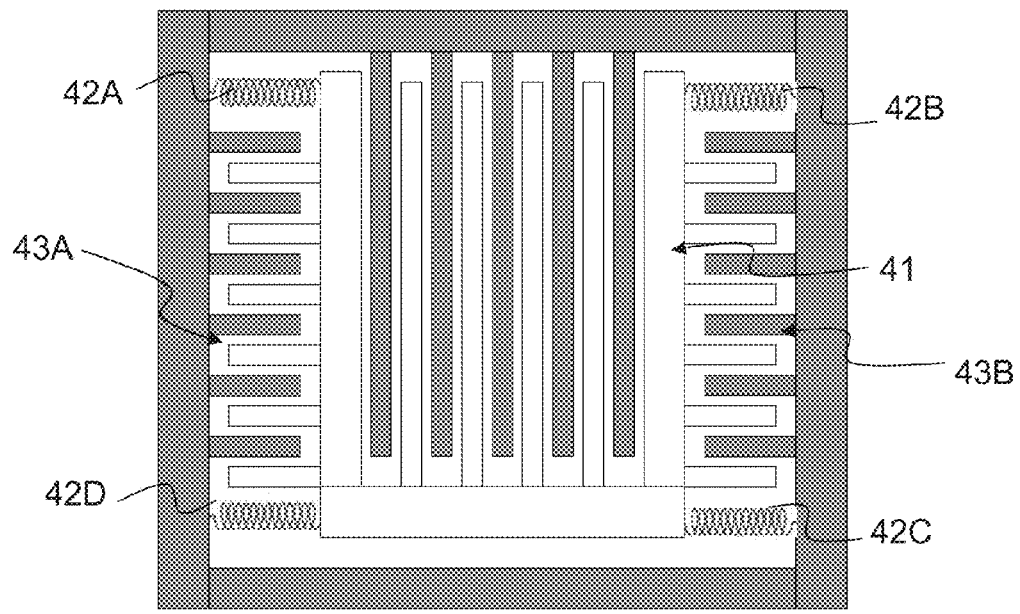
FIG. 4 shows a cross-sectional top view of dynamic grating according to one embodiment of the invention.

FIG. 4a illustrates means for actuation of the grating according to FIG. 3b, herein denoted with reference number 41. The movable portion of the grating has been anchored using springs 42A, 42B, 42C, 42D on two lateral sides of the grating (in the direction of movement of the grating). In addition, there are provided comb drive means 43A, 43B on the sides of the grating to allow for modification of the grating in the desired direction. The comb drive means may be electrostatically or piezoelectrically driven.

Figure 4B:
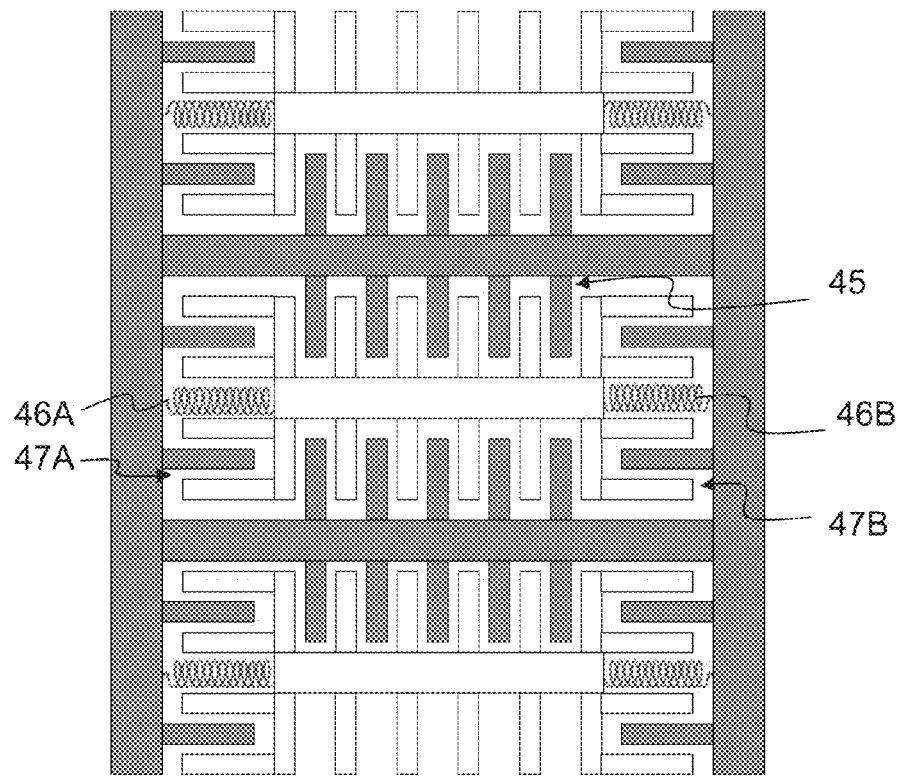

FIG. 4b illustrates a large grating is subdivided into several sub-gratings. Each sub-grating can be actuated independently or in parallel. The grating portion 45 of each sub-grating is in principle similar to shown in. FIG. 3b. Again, there are springs 46A, 46B attached to the movable portion of the grating 45, i.e., the first fingers or the element the fingers are attached to. Comb drive means 47A, 47B are arranged two sides of the grating 45 and functionally connected to the movable portion of the grating 45 to allow for electrostatic moving of the first fingers. It should be noted that the moving can be achieved by other methods, among them piezoelectric, magnetic or thermal actuations. The second fingers are fixed to the substrate. In a similar fashion, every third, fourth, etc, finger can be shifted while leaving the rest of the grating fixed.

By driving the gratings with a time-varying force or by driving them into resonance, it is possible to obtain modulated, dynamic images at high frequencies. By locking-on the grating actuation frequency, a time-varying signal associated with the image can be differentiated from the static background and noise. The method, thus, allows low-dose fast imaging of organic specimens with improved contrast and reduced noise.

Using the comb drive or other suitable drive means, the grating can be moved according to a predefined sequence, like as sinusoidal movement, or even driven into resonance using electrostatic or piezo-actuation.

Spatial modifications of the grating have a strong effect on the resulting interference pattern. The grating distributes the beam's energy spatially (e.g., into bright spots or fringes), and modifying the grating redistributes the beam's energy spatially, e.g., by washing out the interference pattern and eroding the spots intensity or by rebunching the intensities differently. If the grating oscillates at a certain amplitude, every pixel of the detector reads a time-varying signal.

To mention some examples, the phase grating may have a pitch 2-6 µm, for example, and a height of at least 20 µm (depending on the X-ray energy and material of the grating). For 20 keV X-ray energy the Si height required to get π-phase-shift is about 30 µm, which for a pitch of 4 microns (=2 microns wide Si structure) means an aspect ratio of 15. Such structures can be fabricated using modern Si manufacturing techniques.

Figure 5A:
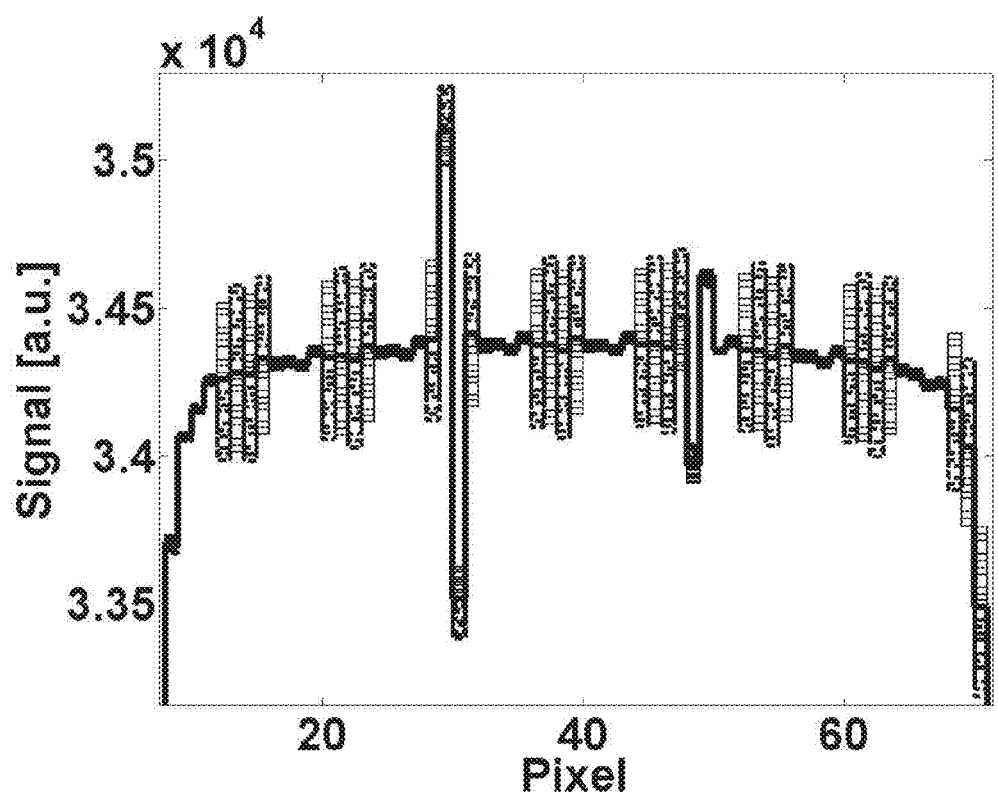
FIG. 5a shows a simulated graph of detector signal at different pixel position in grating-based phase-contrast imaging of an object for different shifts of every second finger of the grating.
Figure 5B:
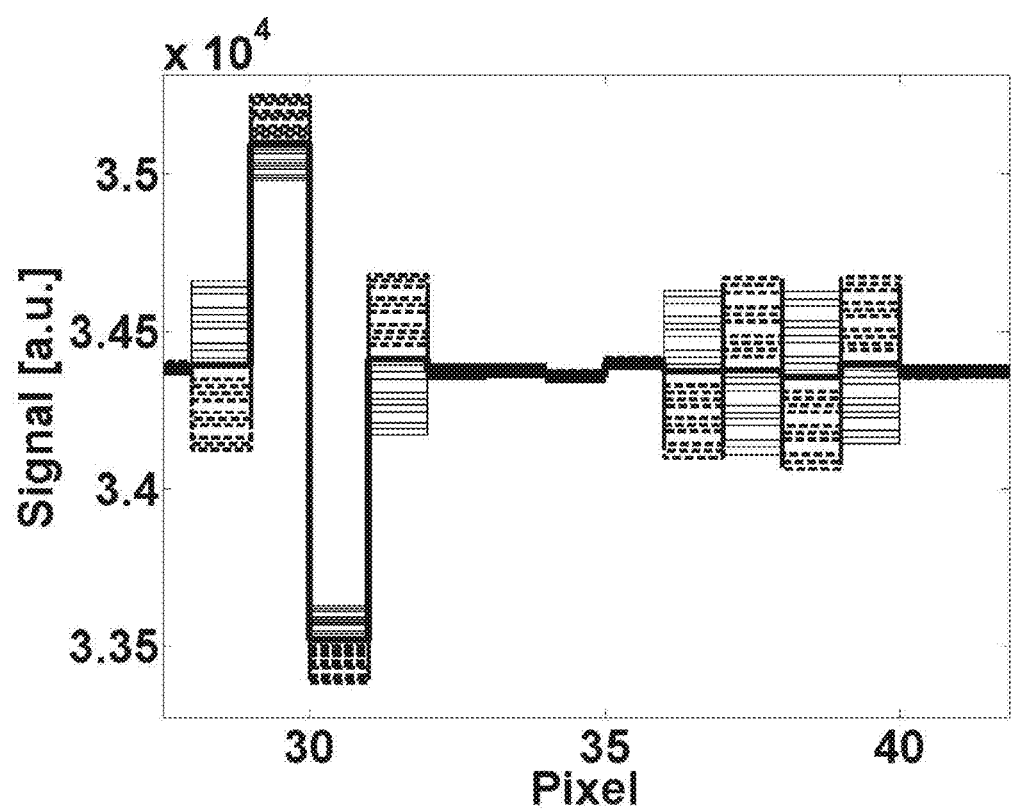

FIG. 5 shows a simulation of the detector read-out for a phase object. Every second finger of the grating was oscillated at 200 nm amplitude. The recorded intensities on some pixels increase when half of the grating is shifted in the positive direction, while on some pixels the intensity decreases. The modulated signal, however, oscillates nearly harmonically about the background signal. The time varying signal on a certain pixel can, therefore, be written as $$V(t) = V_{DC} + A_0 \cos(\omega t).$$

By multiplying this signal with a reference waveform $\cos(\omega t + \varphi)$, one obtains a DC-signal related to the amplitude of the signal variation, $A_0$, and several AC-signals $$V(t)\cos(\omega t + \varphi) == V_{DC}\cos(\omega t + \varphi) + A_0\cos(\omega t)\cos(\omega t + \varphi) == \quad (3)$$

$$V_{DC}\cos(\omega t + \varphi) + \frac{A_0}{2}\cos(\varphi) + \frac{A_0}{2}\cos(2\omega t + \varphi)$$

Figure 6A:
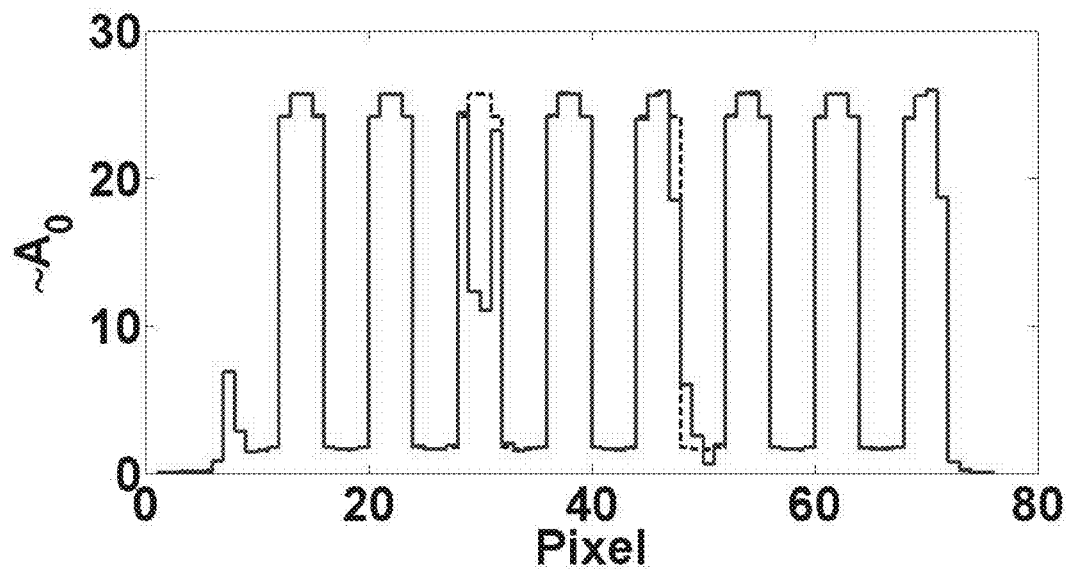
FIG. 6 shows a DC-signal free from background for a $\pi$ rad phase object imaged using a grating with a period of 4 μm. The detector plane is at the distance corresponding to $N=5$ and a) detector's pixels size is 25 μm (corresponds to the situation depicted in FIG. 5), b) detector's pixel size 24 μm.

Filtering the AC-signals results in elimination of the background. By mapping the DC-signal, $\sim|A_0|$, from each pixel, a low-noise, background-free image of the object can be reconstructed. FIG. 6 shows the simulated DC-signal for a detector with 25 and 24 µm pixels. For the 25 µm case, a periodic intensity pattern is formed from the pixels' DC-signals (FIG. 5, FIG. 6a). This is a Moiré pattern, and it is a direct consequence of the mismatch of the grating and the pixel periodicities (4 µm and 25 µm, respectively). Every pixel integrates the intensities from a certain region in space, and if the pixel periodicity does not match the periodicity of the spatial variation of the intensity, a Moiré pattern is formed. The effective period of the modified grating with every second finger shifted is doubled to 8 µm, and the intensity variations in the detector plane induced by the grating modification are expected to happen with the same spatial frequency. The periodicity of the Moiré pattern is thus 25×8=200 µm, or 8 pixels, which is in a perfect agreement with the simulation results (FIG. 5).

In more detail, FIG. 5 shows grating-based phase-contrast imaging of an object for different shifts of every second finger of the grating. Solid line: pixel reading for shifts in the positive direction, dashed line: negative shifts. Maximum amplitude of the shift was 200 nm. The grating period is 4 µm, pixel size is 25 µm. The detector plane is at the distance corresponding to N=5 (see equation above). The phase object is positioned at the centre of the grating and phase-shifts the wavefront by π rad. The object's edges are clearly resolved. The useful signal sits on top of a large background, such that the contrast or visibility is <2%.

Figure 6B:
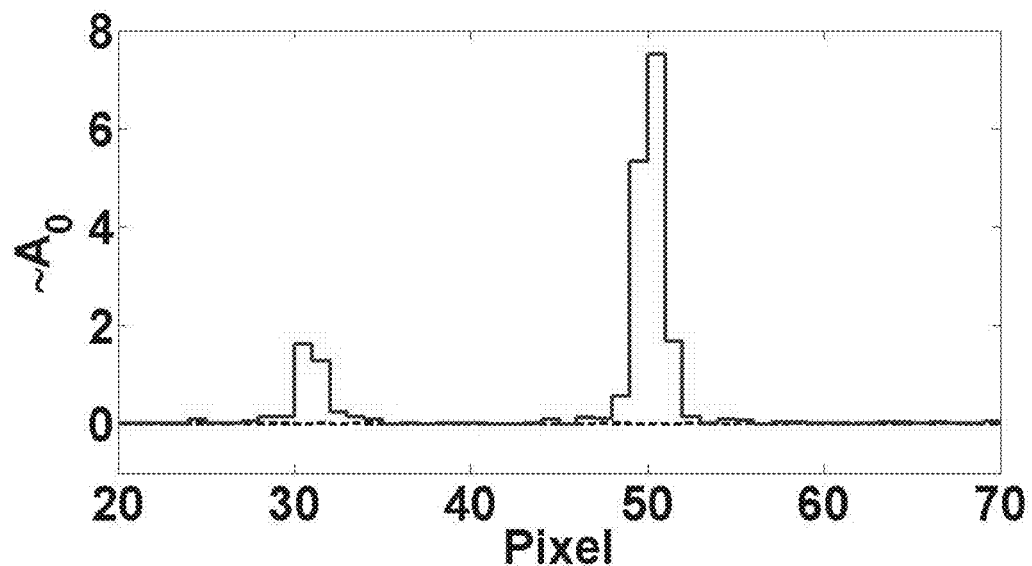

The effects of the phase object is to distort the Moiré pattern (FIG. 6a), and these distortions can be used to retrieve the image of the object. Even though the background is significantly reduced compared to FIG. 5, the image contrast can be hindered by the periodic intensity especially for weak image-related signals. By matching the grating and detector pixel periodicities, the Moiré pattern can be attened out (FIG. 6b). In this case, the modulated signal results only from the asymmetry introduced by the phase object into the wavefront propagation.

MEMS technology enables an infinite number of dynamic grating structure modifications. Some of the examples are listed below:

The phase grating can be shifted or oscillated as a whole. After the shift, the change in the phase gradient due to the object edge coincides with a different location on the grating, such that the propagating wavefront (and consequently the interference pattern) is modified. The achievable mechanical resonance frequency of the grating is reduced by a factor of √2.

Shifting every third finger of the grating triples its effective period. The situation is similar to the previous case with a distinction that the detector pixels' periodicity should be matched with triple the grating periodicity. The resonance frequency increases because only a third of the grating's mass needs to be oscillated. The situation is also interesting because the distances at which the periodic intereference patterns are formed can be matched for both the original and the altered gratings. The first distance where the periodic pattern occurs for the grating with tripled period is, $$\tilde{d}(N=1) = \frac{1}{8}\frac{(3p)^2}{\lambda} = \frac{9}{8}\frac{p^2}{\lambda}.$$

This distance is matched with the distance corresponding to N=9 in the case of the original grating, such that "nodal" intensity points are possible.

Two π/2-phase gratings are positioned one above the other. If both gratings are aligned, the combined grating functions as a single π-phase grating. If one of the grating is shifted with respected to the other, the interference pattern can be significantly altered. When the shift is equal to half the period, the fingers of one grating are aligned with the gaps of the other, and the wave simply propagates through as if there were no grating at all, provided the gap between the two gratings is sufficiently small.

Conventional semiconductor x-ray detectors integrate/accumulate the charges produced by photons arriving at the detector over a certain period of time (integrating over an exposure time). These can be used in connection with the invention, e.g., by synchronizing the read-out of the detector or separate/distinct pixel regions with certain directions of the grating moting to achieve improved contrast and image quality. For instance, every evenly numbered pixel of the detector can be readingout the image while the grating is moved in the positive direction, keeping every oddly numbered pixel idle during this time. Upon reversal of the grating motion into the negative direction every evenly numbered detector pixel is kept idle, while only every oddly numbered pixel integrates the signal. Numerous other grating-detector synchronization scenarios are possible for various grating modifications, e.g., using quarter-cycle of the grating motion and synchronization of various configurations of detector's pixel-regions read-out with the grating motion.

Additional advantages in terms of simplicity of computation may be gained using special detector which measure directly the analog charge at every instance of time (continuously during the exposure), instead of integrating it. In this kind of embodiment, the time-varying charge produced by the photons will follow the time-varying intensity of the light (=number of photons) arriving at the pixels, and the time-characteristic behavior of the intensity of light and hence the analog signal on every pixel will be modulated by the dynamic grating. The amplitude of the modulation will be dependent on the refraction of x-rays inside the object and the amplitude of the grating motion. The amplitude of the detector signal modulation can be extracted by locking-on the specific frequency of the grating modulation, but since this frequency is set by the user, the modulation frequency is readily available. In fact, using lock-in amplifier is not necessary, because it is possible to control the phase difference between the grating modulation and the signal from the pixels. Mixing the modulation signal with the signal from every pixel and filtering the AC-components results in a DC-map of intensities that are proportional to the phase-shift inside the object.

According to one embodiment, the detector configuration comprises, in addition to the actual (semiconductor) detector, means for signal demodulation of the dynamic signal provided by the detector.

According to one embodiment, the detector is configured so that every pixel is able to demodulate the signal that it reads.

According to one embodiment, the pixels of the detector are formed by p-i-n diodes. This can potentially reduce the size of the pixels and improve the resolution compared with detectors frequently used in the prior art. p-i-n-diodes can also in principle provide an analog signal proportional to the intensity of light that shines on them and can be used as the basis of a special detector mentioned above.

The invention claimed is:

1. A method for producing an image of a target using radiation, comprising\
   directing a beam of radiation to the target to produce a modified beam through interaction with the target,
   directing the modified beam to an diffraction grating to produce an interference pattern,
   detecting the interference pattern using a detector, and
   forming an image of the target using the interference pattern measured,
   further comprising modifying the diffraction grating in the plane of the grating during the imaging so that at least two interference patterns are detected using the detector different configurations of the diffraction grating, and
   forming the image of the target using the at least two interference patterns measured
   wherein modifying the diffraction grating comprises modifying the period of the grating by moving at least some lines of the grating with respect to at least some other lines of the grating such that the grating lines maintain their original shape during moving; and
   wherein the grating lines are coplanar.

2. The method according to claim 1, wherein said modifying comprises moving every second, every third or every fourth line of the grating.

3. The method according to claim 1, wherein said modifying comprises translating the grating in the lateral plane of the grating.

4. The method according to claim 1, wherein said the modification comprises oscillation of the diffraction grating.

5. The method according to claim 1, wherein the diffraction grating comprises a microelectromechanically modifiable grating.

6. The method according to claim 1, further comprising reading the detector in synchronization with the modification of the diffraction grating in order to produce at least two different interference images corresponding to said at least two interference patterns, and
   computing the image of the target using said at least two interference images.

7. The method according to claim 1, further comprising integrating the at least two interference patterns on the detector over at least to produce an integrated interference image, and
   computing the image of the target using the integrated interference image.

8. The method according to claim 1, further comprising computing a phase-contrast image of the target, dark field-contrast image of the target, or an absorption-contrast image of the target.

9. The method according to claim 1, further comprising directing the interference pattern essentially directly from the diffraction grating to the detector, without intermediate gratings, and
   computing a phase-contrast and dark-field images of the target.

10. The method according to claim 1, wherein the radiation comprises x-ray radiation.

11. A diffraction grating for phase contrast or dark-field contrast x-ray imaging, comprising
   a layer comprising a periodic pattern of grating lines, the period of the grating being adapted to diffract x-ray wavelengths, wherein
   said layer is a microelectromechanical device layer, and
   the grating further comprises means for changing the periodic configuration of the grating in response to electrical actuation
   wherein a first portion of the grating lines is movable with respect to a second portion of the grating lines for changing the periodic configuration such that the grating lines maintain their original shape during moving; and
   wherein the grating lines are coplanar.

12. The diffraction grating according to claim 11, wherein said means for changing the periodic configuration comprise electrostatic or piezoelectric actuation means.

13. The diffraction grating according to claim 11, wherein the grating lines are arranged in a comb configuration with two comb elements facing each other such that their grating lines are interleaved with each other, and wherein at least one of said comb elements is movable in response to said actuation.

14. The diffraction grating according to claim 11, wherein the grating lines are bendable in response to said actuation for changing the periodic configuration of the grating.

15. An x-ray imaging apparatus capable of producing phase-contrast and/or dark-field contrast images, comprising
   an x-ray source,
   an x-ray detector,
   a diffraction grating arranged between the x-ray source and x-ray detector for producing an interference pattern on the x-ray detector, and
   means for computing an image of the target using the interference pattern measured,
   wherein the diffraction grating comprises
   a layer comprising a periodic pattern of grating lines, the period of the grating being adapted to diffract x-ray wavelengths, wherein
   said layer is a microelectromechanical device layer, and
   the grating further comprises means for moving a first portion of the grating lines with respect to a second portion of the grating lines such that the grating lines maintain their original shape during moving, said moving accomplishing a change in the periodic configuration of the grating; and
   wherein the grating lines are coplanar.

* * * * *